United States Patent
King et al.

(10) Patent No.: US 7,155,278 B2
(45) Date of Patent: Dec. 26, 2006

(54) NEUROSTIMULATION TO TREAT EFFECTS OF SLEEP APNEA

(75) Inventors: Gary W. King, Fridley, MN (US); Marcus J. Mianulli, Plymouth, MN (US); Michael R. S. Hill, Minneapolis, MN (US); Thomas J. Mullen, Ham Lake, MN (US); Roy L. Testerman, New Hope, MN (US); John E. Burnes, Andover, MN (US); Xiaohong Zhou, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 596 days.

(21) Appl. No.: 10/419,405

(22) Filed: Apr. 21, 2003

(65) Prior Publication Data

US 2004/0210261 A1    Oct. 21, 2004

(51) Int. Cl.
*A61N 1/36* (2006.01)

(52) U.S. Cl. .............................. 607/2; 600/26

(58) Field of Classification Search ............. 607/2, 607/117, 43, 48
See application file for complete search history.

(56) References Cited

U.S. PATENT DOCUMENTS

| | | | |
|---|---|---|---|
| 4,830,008 A | 5/1989 | Meer | |
| 5,133,354 A | 7/1992 | Kallok | |
| 5,146,918 A | 9/1992 | Kallok et al. | |
| 5,158,080 A | 10/1992 | Kallok | |
| 5,174,287 A | 12/1992 | Kallok et al. | |
| 5,199,428 A | 4/1993 | Obel et al. ................. | 128/419 |
| 5,215,082 A | 6/1993 | Kallok et al. | |
| 5,233,983 A | 8/1993 | Markowitz | |
| 5,335,657 A | 8/1994 | Terry, Jr. et al. | |
| 5,344,438 A | 9/1994 | Testerman et al. | |
| 5,483,969 A | 1/1996 | Testerman et al. | |
| 5,485,851 A | 1/1996 | Erickson | |
| 5,522,862 A | 6/1996 | Testerman et al. | |
| 5,540,731 A | 7/1996 | Testerman | |
| 5,540,732 A | 7/1996 | Testerman | |
| 5,540,733 A | 7/1996 | Testerman et al. | |
| 5,540,734 A | 7/1996 | Zabara | |
| 5,591,216 A | 1/1997 | Testerman et al. | |
| 5,662,689 A * | 9/1997 | Elsberry et al. ............... | 607/5 |
| 5,895,360 A | 4/1999 | Christopherson et al. | |
| 5,938,596 A | 8/1999 | Woloszko et al. | |
| 5,944,680 A | 8/1999 | Christopherson et al. | |
| 6,021,352 A | 2/2000 | Christopherson et al. | |
| 6,099,479 A | 8/2000 | Christopherson et al. | |

(Continued)

FOREIGN PATENT DOCUMENTS

WO          WO 00/01438 A1          1/2000

*Primary Examiner*—Carl Layno
(74) *Attorney, Agent, or Firm*—Daniel G. Chapik; Paul H. McDowall; Girma Wolde-Michael

(57) ABSTRACT

Neurostimulation is delivered to one or more predetermined locations on or within a patient in order to treat effects of sleep apnea by modulating autonomic nervous activity. Delivery of neurostimulation at predetermined locations can decrease sympathetic nervous activity and/or increase parasympathetic nervous activity, countering the increased intrinsic sympathetic activity associated with apnea-arousal cycles. In some embodiments, neurostimulation is delivered to the spinal cord of the patient via an implanted electrode. In other embodiments, neurostimulation is delivered transcutaneously to the spinal cord or other locations via electrodes located on the surface of the patient. In some embodiments, delivery of neurostimulation is initiated or modified in response to detection of apneas.

57 Claims, 6 Drawing Sheets

U.S. PATENT DOCUMENTS

| | | | |
|---|---|---|---|
| 6,126,611 | A | 10/2000 | Bourgeois et al. |
| 6,132,384 | A | 10/2000 | Christopherson et al. |
| 6,167,304 | A * | 12/2000 | Loos .............................. 607/2 |
| 6,440,090 | B1 | 8/2002 | Schallhorn .................. 600/595 |
| 6,463,327 | B1 | 10/2002 | Lurie et al. |
| 6,526,318 | B1 | 2/2003 | Ansarinia |
| 6,885,888 | B1 * | 4/2005 | Rezai ............................. 607/9 |
| 6,990,376 | B1 * | 1/2006 | Tanagho et al. ............... 607/40 |
| 7,054,689 | B1 * | 5/2006 | Whitehurst et al. ........... 607/40 |
| 2002/0107553 | A1 | 8/2002 | Hill et al. |
| 2002/0143369 | A1 | 10/2002 | Hill et al. |
| 2002/0193697 | A1 | 12/2002 | Cho et al. |
| 2003/0004549 | A1 | 1/2003 | Hill et al. ....................... 607/9 |
| 2003/0040774 | A1 | 2/2003 | Terry, Jr. et al. |
| 2003/0153953 | A1 | 8/2003 | Park et al. ..................... 607/17 |
| 2003/0204224 | A1 * | 10/2003 | Torgerson et al. ............ 607/48 |
| 2004/0249416 | A1 * | 12/2004 | Yun et al. ....................... 607/2 |

* cited by examiner

NEUROSTIMULATION TO TREAT EFFECTS OF SLEEP APNEA

TECHNICAL FIELD

The invention relates to medical devices and, more particularly, to medical devices for treatment of sleep apnea.

BACKGROUND

Sleep apnea generally refers to the cessation of breathing during sleep. It is generally recognized that there are two types of sleep apnea. The more common type of sleep apnea is obstructive sleep apnea (OSA), which is characterized by repetitive pauses in breathing during sleep due to the obstruction and/or collapse of the upper airway, usually accompanied by a reduction in blood oxygen saturation.

The less common type of sleep apnea, central sleep apnea (CSA), refers to a neurological condition causing cessation of substantially all respiratory effort during sleep. One common form of central sleep apnea, commonly known as Cheyne-Stokes respiration (CSR), is characterized by a breathing pattern that begins shallow and infrequent and then increases gradually to become abnormally deep and rapid, before fading away completely for a brief period. Breathing may stop altogether for an extended time period, before the next cycle of shallow breathing begins. CSR is common in patients with congestive heart failure (CHF). Some patients have a combination of OSA and CSA, which is commonly known as mixed sleep apnea.

Cycles of sleep, snoring, obstruction, arousal, and sleep may occur many times throughout the night. The arousal associated with sleep apnea invokes the sympathetic nervous system, which acutely causes increased heart rate and blood pressure. Chronically, episodes of apnea and arousal may lead to systemic hypertension, pulmonary hypertension, ischemic heart disease, stroke, and cardiac arrhythmias. Further, such episodes of apnea and arousal can negatively affect the status, progression, and outcomes of previously existing conditions, such as CHF.

SUMMARY

In general, the invention is directed to techniques for treating effects of sleep apnea with neurostimulation. An implantable medical device delivers neurostimulation to one or more predetermined locations on or within a patient in order to treat effects of sleep apnea, e.g., by modulating autonomic nervous activity. Delivery of neurostimulation at predetermined locations can decrease sympathetic nervous activity and/or increase parasympathetic nervous activity, countering the increased intrinsic sympathetic activity associated with apnea-arousal cycles.

In some embodiments, an implantable medical device delivers neurostimulation to the spinal cord of the patient via one or more implanted electrodes. Electrodes can be located anywhere along the spinal cord. Exemplary locations for electrodes include the region between the T1 and T4 vertebrae and the region between the C1 and C2 vertebrae. In some embodiments, the implantable medical device also delivers neurostimulation to peripheral nerves, such as the vagus nerve. Also, in some embodiments, the implantable medical device delivers cardiac pacing therapy in addition to neurostimulation.

In one embodiment, a pulse generator delivers neurostimulation transcutaneously via electrodes located on the body surface of the patient. Exemplary locations for the electrodes are over peripheral nerves innervated by spinal nerves originating from the above-discussed spinal regions, within the dermatomes associated with these regions, and/or near an ear of the patient.

In another embodiment, delivery of neurostimulation is initiated or modified in response to identification of apneas and/or the arousal associated with apneas. Apneas and associated arousal can be identified using one or more known sensors and detection techniques. An implantable medical device or pulse generator can deliver neurostimulation in response to identification of apnea or arousal when it is determined that the patient is asleep. An implantable medical device or pulse generator can deliver neurostimulation upon determining that the patient is asleep, and modifies the neurostimulation upon identification of an apnea or arousal. Neurostimulation is modified by, for example, changing the location or amplitude of the neurostimulation.

Information relating to identified apneas or arousals may be stored in a memory for use in modifying the programming of an implantable medical device or pulse generator. The information can be used to identify subsequent apneas. The information can also be used as feedback for adjusting characteristics of neurostimulation, e.g., amplitude, for subsequent delivery of neurostimulation in response to a detected apnea or associated arousal.

In some embodiments, an implantable medical device or pulse generator attempts to wake the patient, e.g., in response to detection of a prolonged apnea, to cause the patient to breathe. The implantable medical device or pulse generator can activate an alarm, and/or modify neurostimulation to cause the patient to experience paresthesia.

In one embodiment, the invention is directed to a method for treating effects of sleep apnea in which a spinal cord of a patient is stimulated at a predetermined location to modulate activity of an autonomic nervous system of the patient. The spinal cord may be stimulated to decrease sympathetic nervous activity and/or increase parasympathetic nervous activity. Whether the patient is asleep may be determined, and the spinal cord may be stimulated in response to the determination. A signal from a sensor that indicates a physiological parameter of the patient associated with apnea or arousal resulting from apnea may be received. Apnea and/or arousal may be identified based on the signal. The spinal cord may be stimulated in response to the identification.

In another embodiment, the invention is directed to a system for treating effects of sleep apnea that includes an electrode or electrodes located at a predetermined site or sites proximate to a spinal cord of a patient and a processor. The processor controls delivery of stimulation to the spinal cord via the electrode or electrodes to modulate activity of an autonomic nervous system of the patient. The system may include a sensor, or a patient activator/programmer used to indicate when the patient is asleep, and the processor may control delivery of stimulation in response to determining that the patient is asleep. The system may also include a sensor to generate a signal that indicates a physical parameter of the patient that is associated with apnea or arousal resulting from apnea, and the processor may identify apnea and/or arousal based on the signal. The processor may control delivery of stimulation in response to the identification of the apnea and/or arousal. The system may include an additional electrode or electrodes used to provide pacing pulses to the heart of the patient, and the processor may control or modify delivery of pacing pulses to the heart based on the detected apnea and/or arousal.

In another embodiment, the invention is directed to a method for treating effects of sleep apnea in which neural tissue is transcutaneously stimulated at a predetermined location to modulate activity of an autonomic nervous system of the patient. Whether the patient is asleep may be determined, and the neural tissue may be stimulated in response to the determination. A signal from a sensor that indicates a physiological parameter of the patient associated with apnea and/or arousal resulting from apnea may be received. Apnea and/or associated arousal may be identified based on the signal. The neural tissue may be stimulated in response to the identification.

In another embodiment, the invention is directed to a system that includes an electrode or electrodes located at a predetermined site on the body surface of a patient and a processor. The processor controls transcutaneous delivery of stimulation from the electrode to neural tissue of the patient to modulate activity of an autonomic nervous system of the patient. The system may include a user interface, and the patient may indicate that the patient intends to sleep via the user interface. The processor may control delivery of stimulation in response to determining that the patient is asleep, e.g., upon expiration of a timer. The system may also include a sensor to generate a signal that indicates a physical parameter of the patient that is associated with apnea and/or arousal resulting from apnea, and the processor may identify apnea and/or arousal based on the signal. The processor may control delivery of stimulation in response to the identification of the apnea and/or arousal.

In another embodiments, the invention is directed to a system comprising means for stimulating a spinal cord of a patient at a predetermined location to modulate activity of an autonomic nervous system of the patient. The means for stimulating the spinal cord may comprise means for transcutaneously stimulating nerves that provide a path to the spinal cord.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
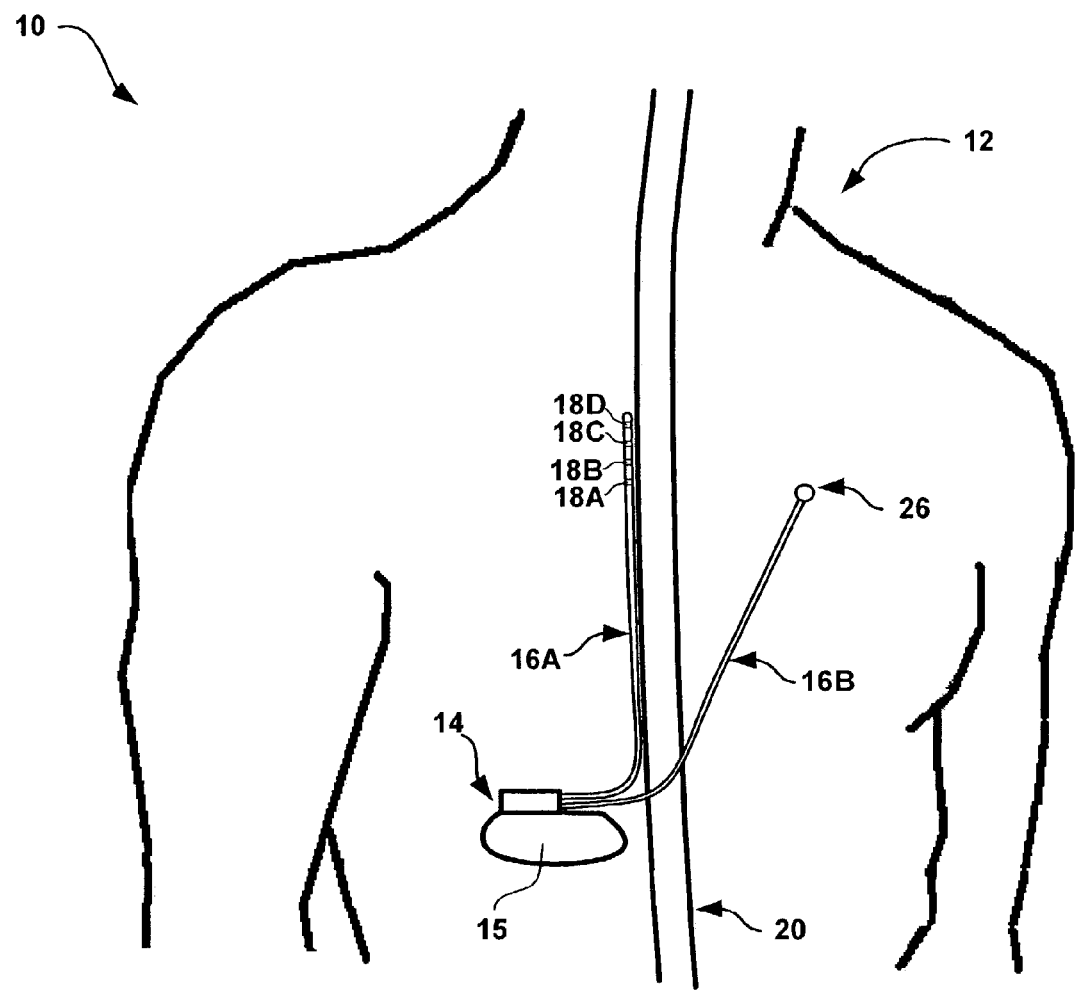
FIG. 1 is a perspective diagram illustrating an example system for treating effects of sleep apnea of a patient.
Figure 1:
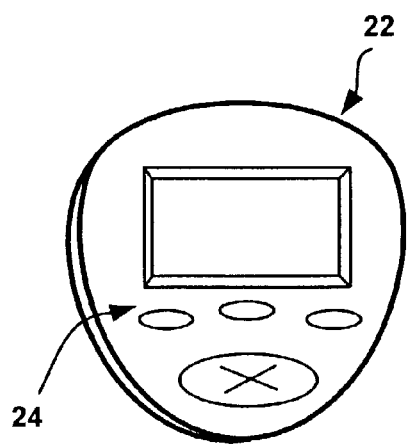

FIG. 1 is a perspective diagram illustrating an example system 10 for treating effects of sleep apnea of a patient 12. As shown in FIG. 1, system 10 includes an implantable medical device (IMD) 14 implanted within patient 12. IMD 14 is coupled to leads 16A and 16B (collectively "leads 16").

Lead 16A includes electrodes 18A–D (collectively "electrodes 18"). Lead 16A is implanted within patient 12 such that electrodes 18 are located proximate to spinal cord 20 of patient 12. IMD 14 stimulates spinal cord 20 at a predetermined location proximate to electrodes 18 by, for example, generating an electrical stimulation waveform delivered to spinal cord 20 via lead 16A and electrodes 18. In some embodiments, electrodes 18 are ring electrodes coupled to IMD 14 via coiled conductors within lead 16A, as is known in the art. In some embodiments, system 10 includes two or more leads 16 coupled to IMD 14, each lead including one or more electrodes 18 for delivery of neurostimulation to spinal cord 20

IMD 14 stimulates spinal cord 20 to treat effects of sleep apnea by modulating activity of the autonomic nervous system (not shown) of patient 12. In general, an apnea and the subsequent arousal associated with the apnea cause increased activation of the sympathetic branch of the autonomic nervous system, which in turn leads to acute increases in heart rate and blood pressure. Over time, these cycles of apnea and arousal may lead to systemic hypertension, and may lead to or accelerate the progression of CHF. For these and other reasons, effective treatment of apnea is highly desirable.

Stimulation of spinal cord 20 can act to reduce sympathetic activity in order to treat apnea. Stimulation of spinal cord 20 can also act to increase parasympathetic activity in order to treat apnea. In general, systemic responses of the autonomic nervous system are a function of the relative strengths, e.g., balance, of the activity of the sympathetic and parasympathetic branches. Therefore, IMD 14 stimulates spinal cord 20 to ameliorate the negative physiological impact associated with apnea-arousal cycles by modulating activity of the autonomic nervous system to reduce prominence of sympathetic activation associated with apnea-arousal cycles.

The effect of stimulation depends on the location where spinal cord 20 is stimulated. In some embodiments, at least one of electrodes 18 is located proximate to the region of spinal cord 20 between the T1 and T4 vertebrae (not shown) of patient 12. In that case, IMD 14 delivers stimulation to this region of spinal cord 20 to reduce the sympathetic activity of nerves originating in this region that innervate the heart (not shown) of patient 12 and the blood vessels that supply the myocardium. The reduction in sympathetic outflow to the heart and surrounding blood vessels can reduce the increase in heart rate and blood pressure that would otherwise result from an apnea-arousal cycle.

Further, delivery of stimulation between the T1 and T4 vertebrae by IMD 14 affects ascending pathways to the cardiorespiratory centers of the brainstem (not shown) of patient 12. Stimulation of these ascending pathways increases parasympathetic outflow via the vagus nerve (not shown) of patient 12, which can further reduce heart rate and blood pressure, e.g., cause vasodilation. Stimulation of these ascending pathways also increases parasympathetic outflow via cranial nerves (not shown) of patient 12, such as the glossopharyngeal nerve, which may lessen obstructive sleep apnea (OSA) by influencing coordination of upper airway muscle groups, such as the pharyngeal muscles. Increased parasympathetic outflow via cranial nerves also affects the hypoglossal nerve, which can lessen OSA by improving the position of the tongue (not shown) of patient 12.

In some embodiments, at least one of electrodes 18 is located proximate to the region of spinal cord 20 between the C1 and C2 vertebrae. In that case, IMD 14 delivers stimulation to this region of spinal cord 20 to directly increase parasympathetic activity of the vagus nerve and cranial nerves, as described above, and to affect lower spinal cord sites that control the sympathetic outflow. In some embodiments, IMD 14 stimulates spinal cord 20 at two or more locations, and the invention is not limited to stimulation of spinal cord 20 at any particular location.

IMD 14 can determine when patient 12 is asleep, and stimulate spinal cord 20 based on that determination. In order to determine when patient 12 is asleep, IMD 14 can include one or more sensors that generate signals as a function of the activity and/or posture of patient 12. In such embodiments, IMD 14 determines when patient 12 is asleep based on the signal. IMD 14 can also have an acoustic sensor, to indicate when snoring starts, and can determine whether patient 12 is asleep based on the presence of snoring.

System 10 can include patient activator (not shown) that magnetically activates a switch within IMD 14 or a patient programmer 22 that communicates with IMD 14 via RF telemetry, as is known in the art. Programmer 22 includes a user interface 24, which may, as illustrated in FIG. 1, include a display and input keys. In some embodiments where IMD 14 determines when patient 12 is asleep, IMD 14 receives an indication from patient 12 that patient 12 intends to sleep via the activator or programmer 22, and determines when patient 12 is asleep based on the indication. In one example, IMD 14 can initiate a timer in response to receiving an indication that the patient intends to sleep. In that case, IMD 14 can determine that the patient is asleep upon expiration of the timer. The length of the timer may be programmed by a physician based on the patient's sleep habits. In other embodiments, a spouse or caretaker of patient 12 can activate the IMD 14 when the spouse or caretaker determines that patient 12 is asleep.

In some embodiments, IMD 14 identifies apnea, or identifies the arousal resulting from apnea, and stimulates spinal cord 20 in response to the identification. Lead 14B includes a sensor 26 that detects a physiological parameter of patient 12 associated with sleep apnea or arousal. IMD 14 identifies apnea or arousal based on the signal conducted from sensor 26 through lead 16B. For example, sensor 26 can take the form of an acoustical sensor, and IMD 14 can detect apnea based on a prolonged period without snoring, e.g., an apnea, after a period during which patient 12 was snoring.

Sensor 26 can take the form of a pressure sensor, such as a capacitive pressure transducer, that generates a signal as a function of the absolute pressure where sensor 26 is located. Sensor 26 may be located in the thoracic cavity, in a blood vessel within the thoracic cavity, or in a chamber of the heart of patient 12. IMD 14 can detect apnea based on increases in blood pressure or intracardiac pressure, or based on characteristics of respiration of patient 12 detected based on changes in the pressure at any of these locations.

Sensor 26 can take the form of one or more electrodes located within the thoracic cavity of patient 12 for detecting impedance. In such embodiments, IMD 14 detects apnea based on respiration of patient 12 as detected via changes in the thoracic impedance. In such embodiments, IMD 14 may monitor frequency, depth, pattern, and variability of respiration. Further, in such embodiments, IMD 14 may detect Cheyne-Stokes rhythm (CSR), or may detect cessation of respiration. In other embodiments, sensor 26 takes the form of one or more electrodes to sense electrical activity of nerves or muscles associated with respiration, such as the phrenic nerve (not shown) or diaphragm (not shown) of patient 12, and IMD 14 monitors respiration of patient 12 based on the electrical activity.

In other embodiments, sensor 26 takes the form of an optical or electrochemical sensor to detect the concentration of a gas within the blood. In such embodiments, sensor 26 generates a signal as a function of the concentration of one or both of oxygen and carbon dioxide in the blood of patient 12. In such embodiments, IMD 14 detects apnea based on a decreased concentration of oxygen and/or an increased concentration of carbon dioxide in the blood of patient.

In still other embodiments, system 10 includes one or more leads 16 (not shown) with unipolar or bipolar pacing/sensing electrodes located within or proximate to the heart of patient 12. The electrodes can be located in one or more chambers of the heart of patient 12, or can be located epicardially. Sensing electrodes can also be located near or integral with a housing 15 of IMD 14. Such electrodes function as sensors that allow IMD 14 to sense electrical activity attendant to depolarization and repolarization of the heart of patient 12.

In such embodiments, IMD 14 measures one or more of heart rate, heart rate variability, heart rate turbulence, Q-T intervals, and S-T intervals based on the signals received from the electrodes, and identifies arousal associated with apnea based on the measurements. Heart rate variability can include atrial rate variability, ventricular rate variability, or atrio-ventricular interval variability. Various embodiments of system 10 include pacing/sensing leads and electrodes in addition to or instead of lead 16B and sensor 26. In some embodiments, IMD 14 can sense electrical activity attendant to depolarization and repolarization of the heart via electrodes 18 of lead 16A located near spinal cord 20, can detect apnea and/or arousal based on the electrical activity as described above, and need not include an additional lead 16B and sensor 26.

In cases where system 10 includes leads 16 with pacing/sensing electrodes located within or proximate to the heart of patient 12, IMD 14 can provide cardiac pacing therapy in addition to stimulating spinal cord 20. IMD 14 can provide pacing therapy according to any of numerous pacing modalities known in the art. For example, in some embodiments, IMD 14 is coupled to three pacing/sensing leads located within or proximate to the right atrium, right ventricle and left ventricle, respectively, and provides cardiac resynchronization therapy using techniques known in the art.

Various embodiments of system 10 identify apnea and/or arousal using one or more of the embodiments of sensor 26 and techniques described above. Furthermore, various embodiments of system 10 identify apnea and/or arousal using one of more of the sensors and techniques described in commonly-owned pending provisional U.S. patent application Ser. No. 10/419,467 filed on even date hereof (based upon provisional application Ser. No. 60/439,303 filed 10 Jan. 2003) and entitled, "Method and Apparatus for Detecting Respiratory Disturbances;" and provisional U.S. patent application Ser. No. 10/419,404 filed on even date hereof (based upon provisional U.S. patent application Ser. No. 60/439,409 filed 10 Jan. 2003) and entitled, "Apparatus and Method for Monitoring for Disordered Breathing" the contents of both disclosures are hereby incorporated as if fully set forth herein.

System 10 can include additional leads 16 and electrodes 18 (not shown), and IMD 14 can additionally stimulate peripheral nerves or neural ganglia to modulate the autonomic nervous system activity. For example, in some embodiments, system 10 includes a lead 16 and electrode 18, such as a cuff electrode known in the art, to stimulate the vagus nerve of patient 12. Stimulation of the vagus nerve increases parasympathetic output to the heart.

Figure 2:
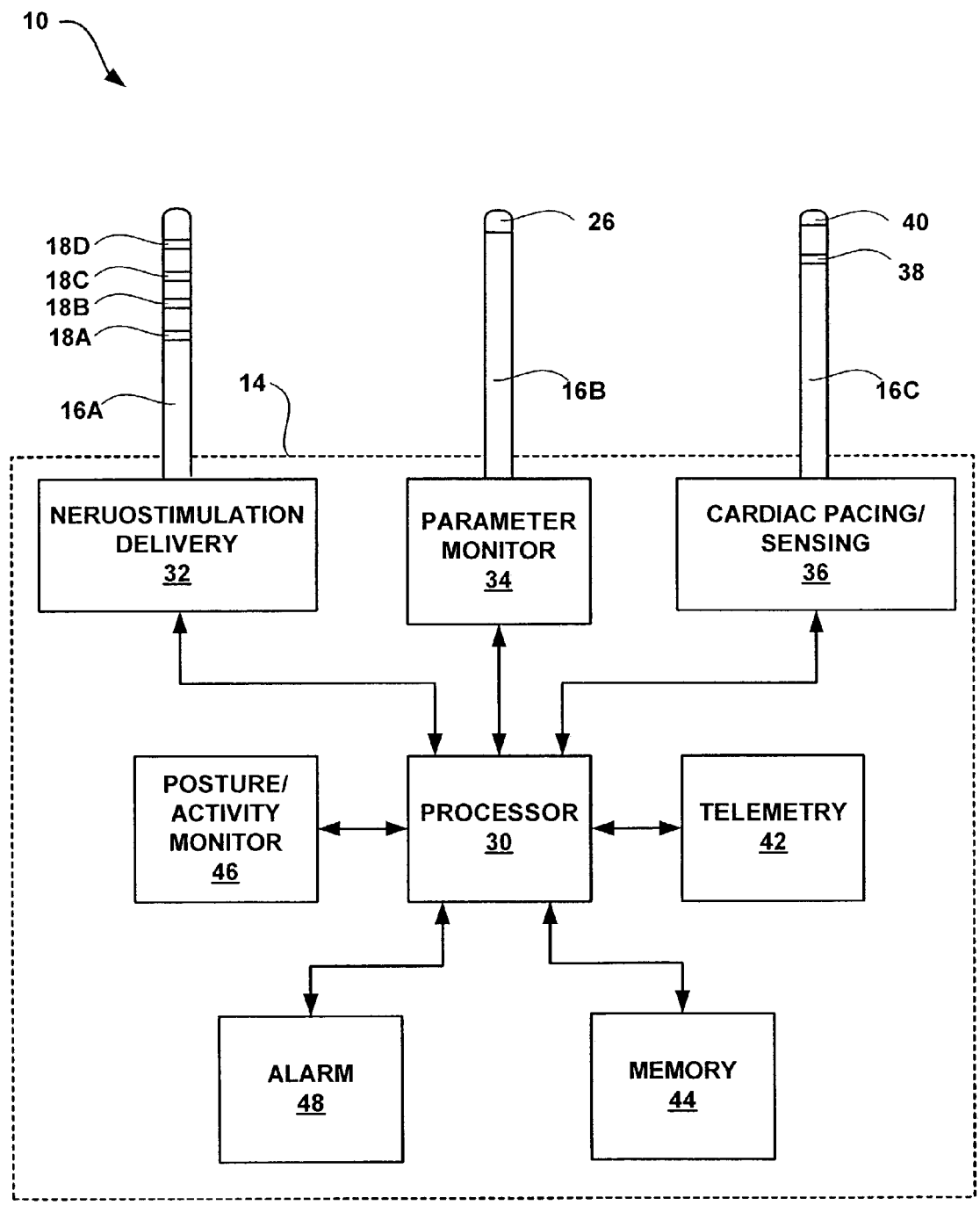
FIG. 2 is a block diagram illustrating the system of FIG. 1 in greater detail.

FIG. 2 is a block diagram illustrating system 10 in greater detail. As shown in FIG. 2, IMD 14 includes a processor 30 coupled to a neurostimulation delivery circuit 32, which is in turn coupled to electrodes 18 via lead 16A. Neurostimulation delivery circuit 32 includes circuits capable of producing stimulation signals of one or more waveform types coupled to a power source. Neurostimulation delivery circuit 32 can, for example, provide direct current, sinusoidal, or pulsed stimulation. In exemplary embodiments, neurostimulation delivery circuit 32 includes capacitive elements to store energy for delivery as pulses, and switches to couple the capacitive elements to selected electrodes 18 and control the features of the pulses. In general, however, neurostimulation delivery circuit 32 is subject to a wide variety of implementation specific configurations for generation of the pulses.

Processor 30 controls the waveform and amplitude of stimulation delivered by neurostimulation delivery circuit 32, and the electrodes 18 by which neurostimulation delivery circuit 32 delivers the stimulation. Amplitude may be voltage or current amplitude. In the case of pulsed stimulation, processor 30 controls the rate and width of pulses. In some embodiments, neurostimulation delivery circuit 32 is coupled to two or more leads 16, each lead including one or more electrodes 18 for delivery of stimulation to spinal cord 20 (FIG. 1). In exemplary embodiments, processor 30 controls neurostimulation delivery circuit 32 to deliver neurostimulation in the from of a 50 Hz pulse train, with 200 microsecond pulse widths and 0–10 V pulse amplitudes. The invention, however, is not limited to these specific pulse train frequencies, pulse widths or pulse amplitudes, or even to delivery of periodic stimulation.

IMD 14 also includes a parameter monitor 34 coupled to sensor 26 through lead 16B. In general, parameter monitor 34 receives a signal from sensor 26 and provides an indication of a measurable physiological parameter of patient 12 related to apnea and/or arousal to processor 30 based on the signal. Processor 30 can identify apnea and/or arousal based on the information received from parameter monitor 34.

In embodiments where sensor 26 is an absolute pressure sensor, parameter monitor 34 is a pressure monitor, such as the Chronicle™ Implantable Hemodynamic Monitor manufactured by and commercially available from Medtronic, Inc. of Minneapolis, Minn., which communicates absolute pressure at the location of sensor 26 to processor 30. Similarly, in embodiments where sensor 26 is a blood gas sensor or electrodes to detect electrical activity of muscles or nerves, parameter monitor 34 includes appropriate circuitry for processing the signal to provide a value for the physiological parameter of interest to processor 30. In some embodiments, IMD 14 includes multiple parameter monitors 34, each parameter monitor 34 coupled to one or more sensors 26 via one or more leads 16.

IMD 14 can include cardiac pacing/sensing circuitry 36. As discussed above, system 10 can include pacing/sensing electrodes 38 and 40 instead of or in addition to sensors 26, and pacing/sensing electrodes 38 and 40 can be used as a sensor to sense signals attendant to the depolarization and repolarization of the heart of patient 12. Pacing/sensing electrodes 38 and 40 are illustrated in FIG. 2 as coupled to cardiac pacing/sensing circuitry 36 via a lead 16C. Some embodiments of system 10 include two or more pairs of pacing/sensing electrodes, each pair coupled to cardiac pacing/sensing circuitry 36 by a lead. Further, in some embodiments, pacing/sensing circuitry 36 can be coupled to one or more electrodes near or integral with housing 15 (FIG. 1) of IMD 14, or to electrodes 18 on lead 16A located near spinal cord 20, as discussed above.

Cardiac pacing/sensing circuitry 36 includes known circuitry for detecting events or signals within an electrogram signal sensed by electrodes 38 and 40, such as automatic gain controlled amplifiers providing adjustable sensing thresholds as a function of measured R-wave, P-wave, or T-wave amplitude, and timing circuits to determine R-R intervals and other intervals of interest which are communicated to processor 30. Processor 30 can determine apnea based on these intervals.

In some embodiments, cardiac pacing/sensing circuitry 36 also includes circuitry for delivering pacing pulses to the heart of patient via electrodes 38 and 40. In such embodiments, cardiac pacing/sensing circuitry 36 includes one or more output circuits coupled to the timing circuits, which are capable of storing energy for delivery in the form of a pacing pulse when directed by the timing circuitry. Through communication with the timing circuitry, processor 30 controls the delivery of pacing therapy. For example, processor 30 can control the intervals used by timing circuitry to determine when to cause delivery of pacing pulses, e.g., escape intervals. Processor 30 can also control the amplitude and width of pacing pulses.

IMD 14 may include a telemetry circuit 42 for RF communication with programming devices, such as patient programmer 22 (FIG. 1). As mentioned above, in some embodiments, processor 30 determines whether patient 12 is asleep. In such embodiments, patient 12 may indicate an intention to sleep using programmer 22. Processor 30 receives the indication from patient via telemetry circuit 42 and initiates a timer. When the timer expires, processor initiates stimulation, or attempts to identify apneas to initiate stimulation upon identification. In various embodiments, the value of the timer is stored in a memory 44, or entered by patient 12 via programmer 22. In some embodiments, IMD 14 includes a switch (not shown) instead of or in addition to telemetry circuit 42, and patient 12 indicates an intention to sleep by magnetically activating the switch using a patient activator or an activator used by a spouse or caretaker of patient 12.

IMD 14 can additionally or alternatively include a posture and/or activity monitor 46 that provides information to processor 30 indicating the posture and/or activity of patient 12. In such embodiments, processor 30 determines whether patient 12 is asleep based on indicated posture and activity. Posture and/or activity monitor 46 includes a sensor that generates a signal as a function of posture and/or activity, such as a piezoelectric accelerometer or a microelectromechanical sensor (MEMS), and circuitry to process that signal and indicate posture and/or activity to processor 30 based on the signal. Activity can also be determined based on below-threshold heart rate or respiration rate values IMD 14 can include an alarm 48. Alarm 48 is detectable by patient 12, or a spouse or caretaker of patient 12, e.g. audibly or via vibration. Processor 30 activates alarm 48 to wake patient 12 in order to cause patient 12 to breathe, e.g., upon identification of an extended period of apnea.

Memory 44 stores program instructions that control the behavior of processor 30. In some embodiments, memory 44 stores algorithms and threshold values used to determine when patient 12 is asleep and to identify apneas. In some embodiments, memory 44 stores information used to select electrodes, waveforms, stimulation amplitudes and durations, and, where stimulation is delivered to spinal cord as pulses, pulse widths and rates. In cases where IMD 14 provides cardiac pacing therapy, memory 44 stores information and algorithms used to control delivery of cardiac pacing to the heart of patient 12.

Memory 44 can include any of one or more of a variety of media, such as random access memory (RAM), read only memory (ROM), or electrically erasable programmable read only memory (EEPROM). In various embodiments, processor 30 includes one or more microprocessors, digital signal processors (DSPs), field programmable gate arrays (FPGAs), application specific integrated circuits (ASICs), discrete logic components, or the like. Where IMD 14 provides cardiac pacing therapy, processor 30 may include at least two processors in communication via a data bus, with one processor controlling delivery of stimulation to spinal cord 20 and another processor controlling delivery of cardiac pacing therapy.

Figure 3:
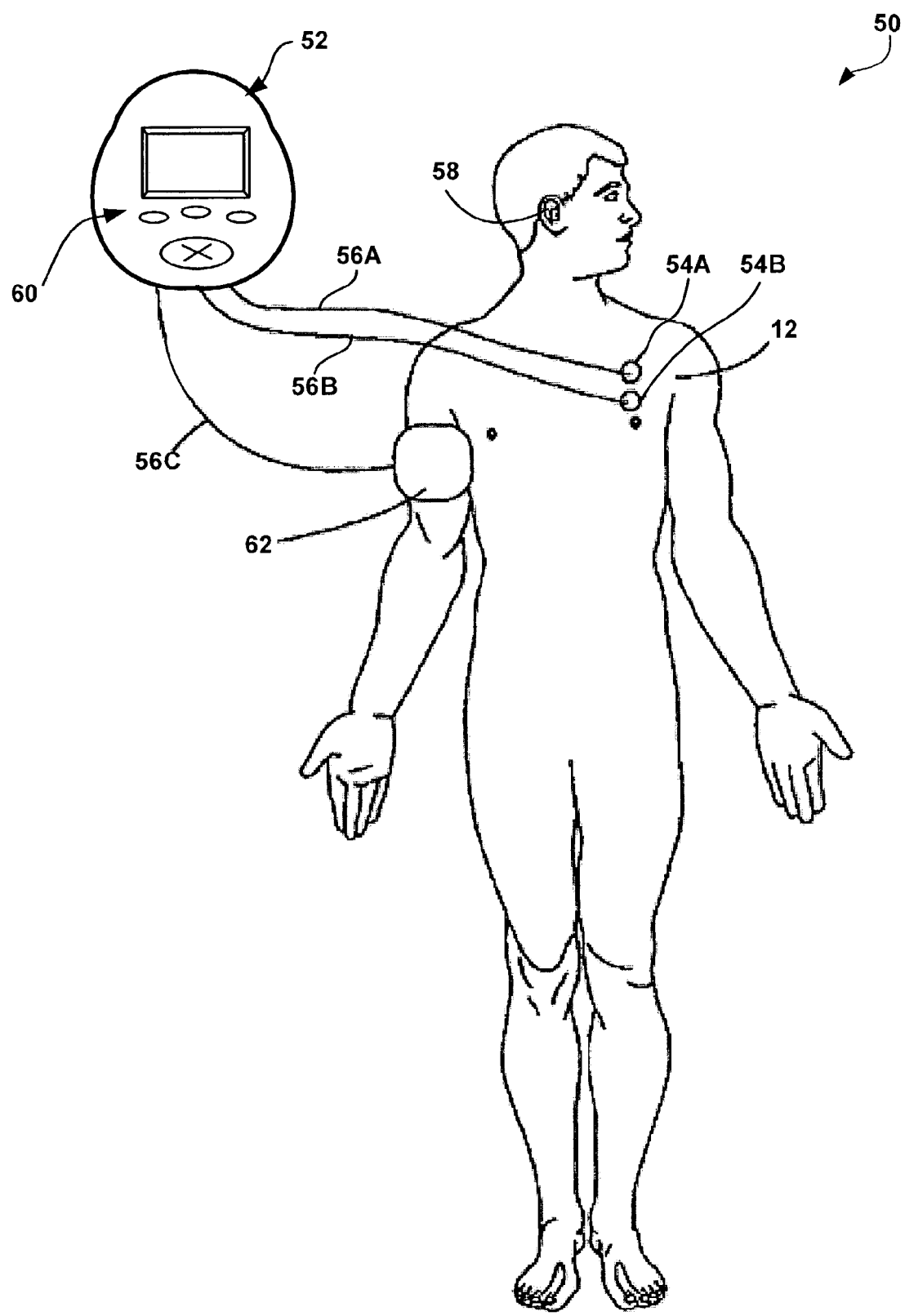
FIG. 3 is a perspective diagram illustrating another example system for treating effects of sleep apnea of a patient.

FIG. 3 is a perspective diagram illustrating another example system 50 for treating effects of sleep apnea of patient 12 by modulating activity of the autonomic nervous system of patient 12. As shown in FIG. 3, system 50 includes a pulse generator 52, and transcutaneous electrodes 54A and 54B (collectively "electrodes 54") coupled to pulse generator 52 via leads 56A and 56B, respectively. Electrodes 54 correspond to any of a variety of known transcutaneous electrode designs, and, in some embodiments, are fixed to the skin of patient 12 with an adhesive patch.

Pulse generator 52 transcutaneously stimulates neural tissue via electrodes 54 to modulate activity of the autonomic nervous system of patient 12. In some embodiments, pulse generator transcutaneously stimulates muscles and/or nerves connected to specific levels of the spinal cord of patient 12. In such embodiments, electrodes 54 are located at a predetermined area along the chest, arm or neck of patient 12. Transcutaneous stimulation in the regions discussed above, i.e., of tissue innervated by nerves between T1 and T4 or between C1 and C2 of the spinal cord, provides a similar effect on sympathetic and/or parasympathetic activity as stimulation via electrodes 16 (FIG. 1) implanted proximate to these spinal cord regions.

In some embodiments, electrodes 54 are located within a dermatome associated with the above-discussed regions, i.e., a region of the body innervated by nerves originating from or projecting to the above-discussed regions of spinal cord 20. Transcutaneous stimulation of neural tissue within the dermatomes associated with the regions discussed above provides a similar effect on sympathetic and/or parasympathetic activity as stimulation via implanted electrodes 16 (FIG. 1) and transcutaneous electrodes at these regions. System 50 can include two or more electrodes 54 at two or more locations, and the invention is not limited to the described locations of electrodes 54. For example, an electrode 54 may be located proximate to an ear 58 of patient 12 to stimulate peripheral nerves near the ear, which can cause increased parasympathetic outflow to the heart (heart) of patient 12 through the vagus nerve (not shown) of patient 12.

Pulse generator 52 can determine whether patient 12 is asleep, and transcutaneously stimulate neural tissue based on the determination. Patient 12, or a spouse or caretaker of patient 12, may also indicate to pulse generator 52 that the patient intends to sleep. In that case, pulse generator 52 can determine that the patient is asleep upon expiration of the timer. The length of the timer may be programmed by a physician based on the patient's sleep habits, or adjusted by the patient.

In some embodiments, pulse generator 52 identifies apneas or arousal associated with apneas, and transcutaneously delivers stimulation based on the identification. System 50 can include a sensor 62 coupled to pulse generator 52 via a lead 56C. Sensor 62 generates a signal as a function of a physiological parameter of patient 12 associated with sleep apnea or arousal, and pulse generator 52 identifies apneas and/or arousals based on the signal.

Sensor 62 can take the form of a blood pressure cuff, or an infrared sensor to detect cutaneous blood gas concentrations. Sensor 62 can also take the form of one or more additional patch electrodes to detect thoracic impedance or electrical activity of the heart of patient 12. Sensor 62 can take the form of an acoustic sensor to detect snoring, as discussed above. System 50 may include two or more sensors 62 and two or more types of sensors 62. Pulse generator 52 can detect apneas and/or arousals according to any one or more known techniques, such as the above-described and above-referenced techniques.

Although not shown in FIG. 3, some embodiments of system 50 include additional patch electrodes located on the chest wall of patient, and pulse generator 52 provides cardiac pacing therapy via the additional electrodes. In some embodiments, electrodes 54 may be used for external pacing when not used to transcutaneously deliver stimulation to neural tissue.

Figure 4:
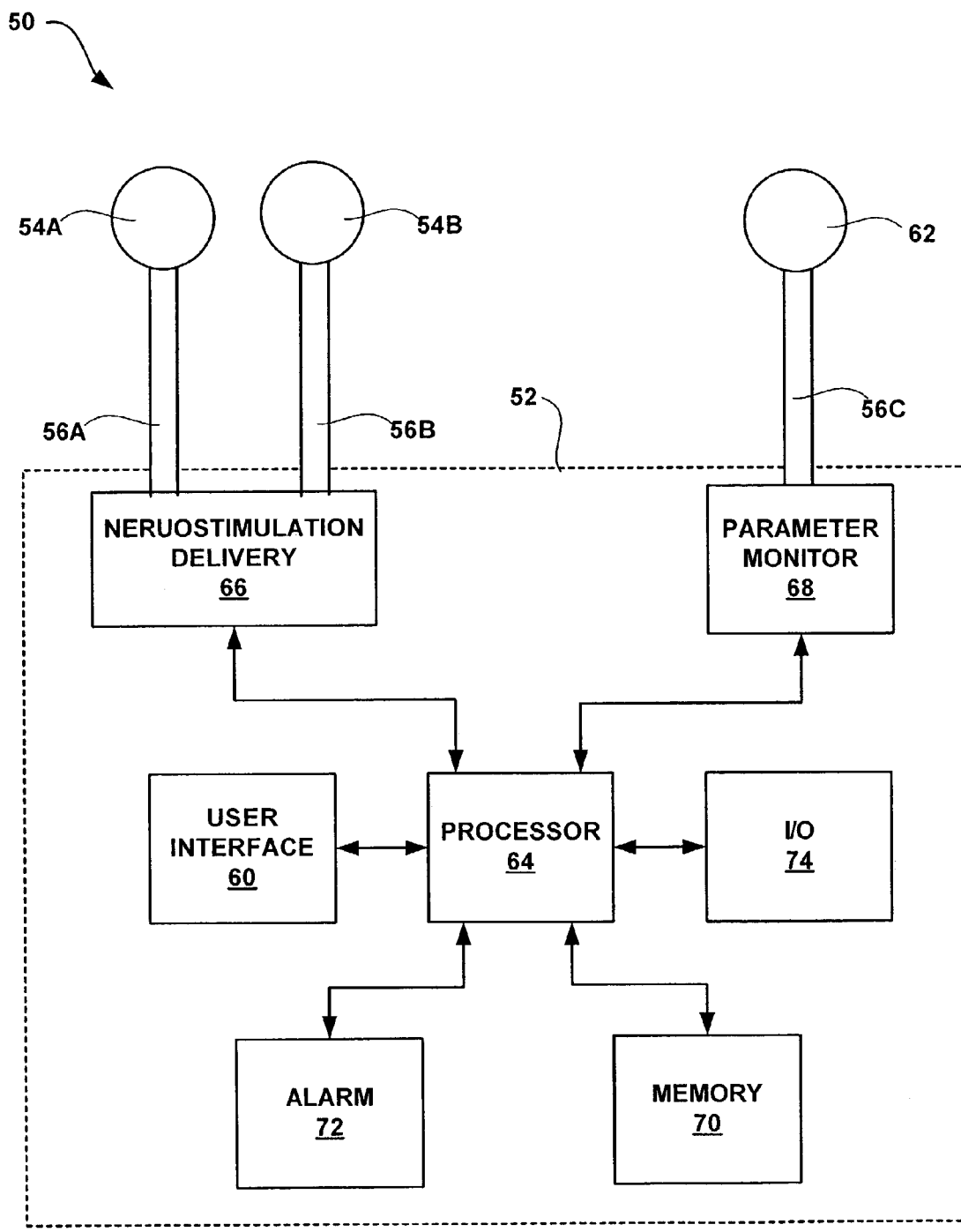
FIG. 4 is a block diagram illustrating the system of FIG. 3 in greater detail.

FIG. 4 is a block diagram illustrating system 50 in greater detail. As shown in FIG. 4, pulse generator 52 includes a processor 64 coupled to a neurostimulation delivery circuit 66, which is in turn coupled to transcutaneous electrodes 54A and 54B via leads 56A and 56B, respectively. Neurostimulation delivery circuit 66 corresponds to and provides substantially the same functionality as neurostimulation delivery circuit 32 (FIG. 2).

Processor 64 controls the waveform and amplitude of stimulation delivered by neurostimulation delivery circuit 66, and the electrodes 54 by which neurostimulation delivery circuit 66 delivers the stimulation. Amplitude may be voltage or current amplitude. In the case of pulsed stimulation, processor 64 controls the rate and width of pulses. In exemplary embodiments, processor 64 controls neurostimulation delivery circuit 66 to deliver neurostimulation in the from of a 50 Hz pulse train, with 200 microsecond pulse widths and 0–10 V pulse amplitudes. However, as discussed above, the invention is not limited to these specific pulse train frequencies, pulse widths or pulse amplitudes, or even to delivery of periodic stimulation.

Pulse generator 52 also includes a parameter monitor 68 coupled to sensor 62 through lead 56C. In general, parameter monitor 68 receives a signal from sensor 62 and provides an indication of a measurable physiological parameter of patient 12 related to apnea or arousal to processor 64 based on the signal. In some embodiments, processor 64 identifies apnea and/or arousal based on the information received from parameter monitor 68. Parameter monitor 68 includes appropriate circuitry for processing signals provided by whichever type or types of sensors 62 are included in system 50 for detection of apnea and/or arousal.

In some embodiments, pulse generator 52 includes a user interface 60 for receiving input from patient 12, or a spouse or caretaker of patient 12, indicating an intention of patient 12 to sleep. Upon receiving the indication, processor 64 initiates a timer, and determines that patient 12 is asleep upon expiration of the timer. The value of the timer may be stored in memory 70, or input by patient 12 via user interface 60. Where the value of timer is stored in memory 70, a physician may program the length of the timer based on the patient's sleep habits.

Some embodiments of pulse generator 52 include an alarm 72. Alarm 72 is detectable by patient 12, or a spouse or caregiver of patient 12, e.g. audibly or via vibration. In such embodiments, processor 64 activates alarm to wake patient 12, or to cause a spouse or caregiver of patient 12 to wake patient 12, to cause patient 12 to breathe, e.g., upon identification of an extended period of apnea.

Pulse generator 52 can be programmable by and communicate with a programming device via an input/output circuit 74. Using a programming device, a physician is capable of programming the behavior pulse generator 52, and collecting any information stored by pulse generator 52. I/O circuit includes appropriate circuitry for communication via wired, RF, infrared, or other communication media.

Figure 5:
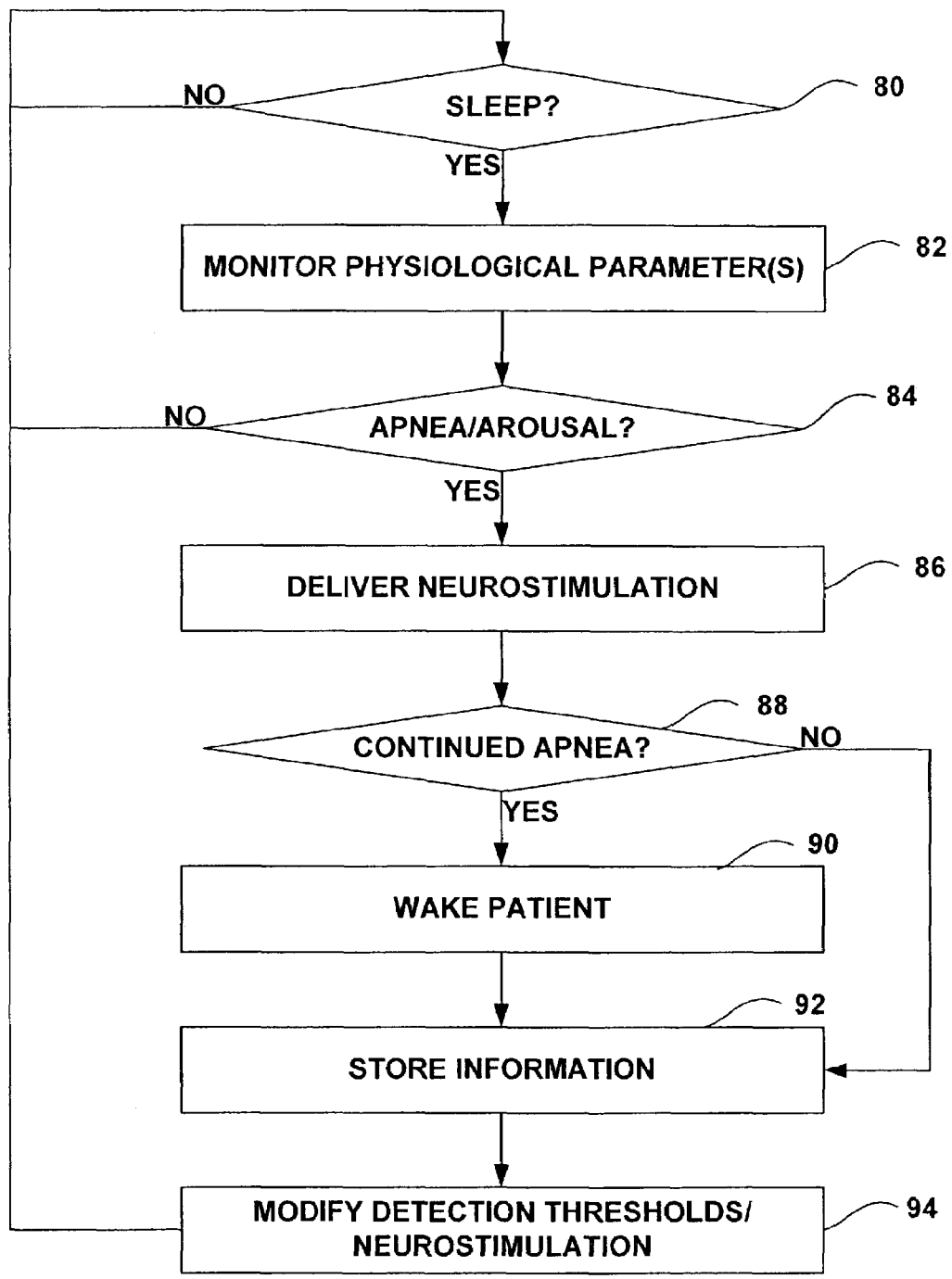
FIG. 5 is a flow diagram illustrating an exemplary mode of operation of a system to treat effects of sleep apnea.
Figure 6:
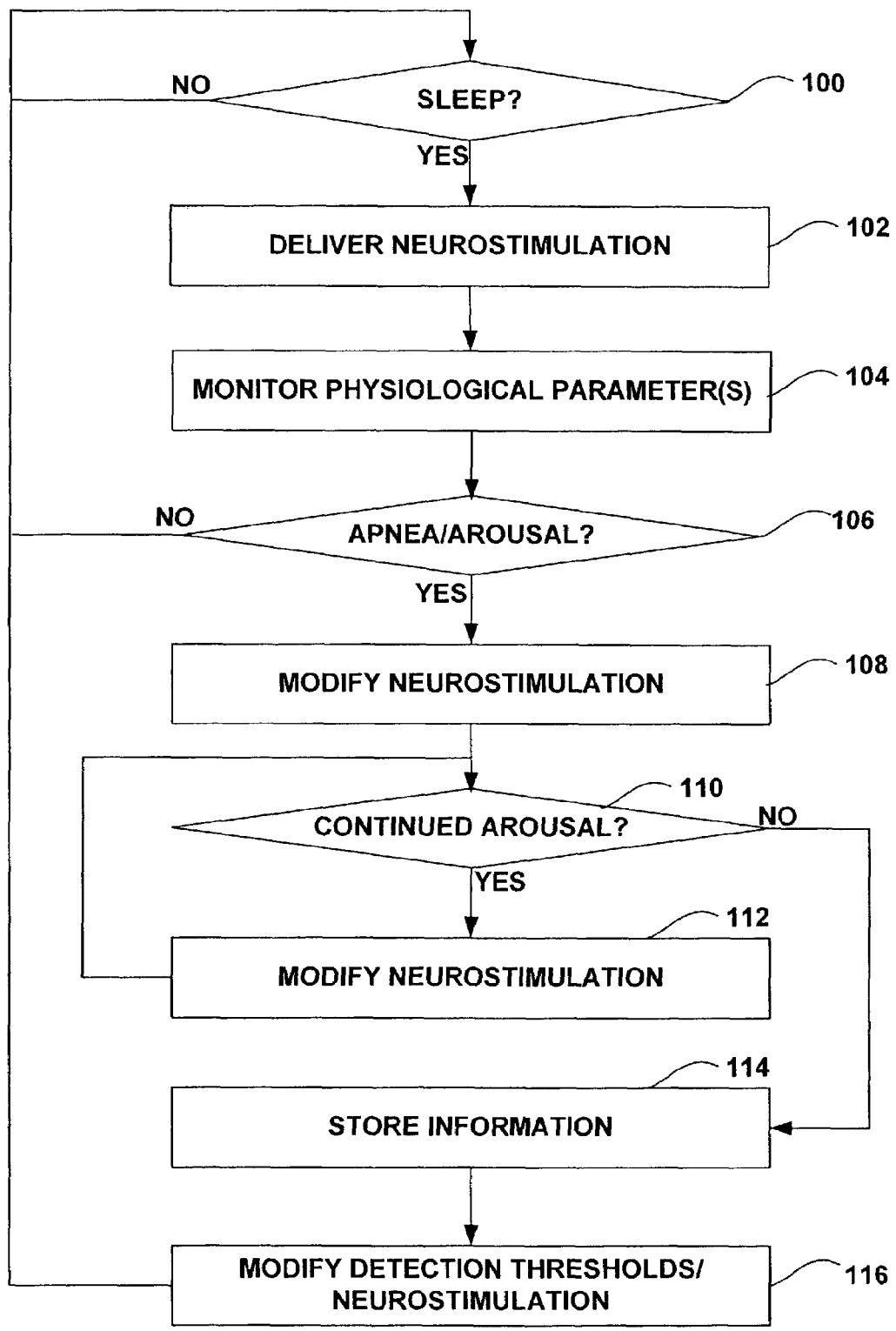
FIG. 6 is a flow diagram illustrating another exemplary mode of operation of a system to treat effects of sleep apnea.

FIGS. 5 and 6 are flow diagrams illustrating exemplary modes of operation of system 10 to treat effects of sleep apnea through the delivery of stimulation to spinal cord 20 of patient 12. It is understood that, in some embodiments, system 50 also operates according to these exemplary modes. However, for ease of description, the exemplary modes of operation illustrated in FIG. 5 and 6 will be described with reference to system 10 only.

As shown in FIG. 5, processor 30 determines whether patient 12 is asleep based on input of patient 12 using programmer 22 and/or a signal generated by posture/activity monitor 46, as described above (80). When processor 30 determines that patient 12 is asleep, processor 30 monitors one or more physiological parameters, e.g., the inputs provided by parameter monitor 34 and/or cardiac pacing/sensing circuit 36 (82). If processor 30 identifies an apnea, or arousal associated with apnea, based on these inputs (84), e.g., using any of the above-discussed or above-referenced techniques for identifying apnea or arousal based on one or more physiological inputs, processor 30 controls neurostimulation delivery circuit 32 to deliver neurostimulation to spinal cord 20 (86). In an exemplary embodiment, IMD 14 delivers stimulation in the form of electrical pulses to spinal cord 20 via an electrode 18 located between the T1 and T4 vertebrae of patient 12.

In some embodiments, stimulation is delivered to spinal cord at multiple locations, and stimulation can also be delivered to a peripheral nerve, such as the vagus nerve. In some embodiments, processor 30 does not determine whether patient 12 is asleep, but instead monitors for apneas and/or arousal whenever activated. Nonetheless, it may be preferred to determine whether patient 12 is asleep to avoid erroneously identifying apneas and/or arousals and stimulating spinal cord 20 when patient 12 is awake and is, for example, exercising.

Processor 30 can determine whether an identified apnea is prolonged (88), e.g., by continuing to monitor the physiological parameters, running a counter during the period that apnea persists, and comparing the counter to a threshold value in memory 44. If apnea is prolonged, processor 30 wakes patient 12 to cause patient to breathe 12 (90). Processor 30 can wake patient 12 by activating alarm 48 and/or controlling neurostimulation delivery circuit 32 to deliver paresthesia-causing stimulation. In other embodiments, processor 30 simply wakes patient 12 upon identification of apnea to cause patient 12 to breathe. The alarm or stimulation used to wake patient 12 may be of an intensity that arouses patient 12 sufficiently to cause patient 12 to breathe, but not so intense as to significantly disturb the sleep of patient 12.

Processor 30 can store information relating to identified apneas in memory 44 (92). Processor 30 can use such information as feedback to improve the efficacy of IMD 14 (94). For example, based on the information processor 30 can adjust thresholds stored in memory 44 that are used to identify apneas or arousal in order to better identify subsequent apneas. Processor 30 can also adjust characteristics of neurostimulation delivered to patient 12 based on the information. For example, processor 30 can control delivery of neurostimulation at an increased amplitude in response to a subsequent apnea or arousal if previous arousals were not suppressed by delivery of neurostimulation at lower amplitudes.

A physician may retrieve the information using a programmer via telemetry circuit 42. The physician can analyze the information, and can possibly make adjustments to thresholds, algorithms, and stimulation characteristics based on the information. The clinician can also make adjustments to other therapies provided to patient 12, such as adjustments to cardiac resynchronization therapy provided to treat congestive heart failure of patient 12, based on the information.

As shown in FIG. 6, in some embodiments of IMD 14, processor 30 determines whether patient 12 is asleep (100), and stimulates spinal cord 20 upon determining that patient 12 is asleep (102). In such embodiments, stimulation delivered to spinal cord prior to identified apneas can decrease the probability of apneas occurring by decreasing sympathetic activity and/or increasing parasympathetic activity. Increasing the relative prominence of parasympathetic activity can promote restful sleep and open the upper airway of patient 12 to lessen the likelihood of OSA.

Processor 30 monitors physiological parameters to identify an apnea or arousal associated with apnea (104). Upon identification of apnea or arousal (106), processor 30 modifies the delivery of stimulation to spinal cord 20 (108). For example, in some such embodiments, processor 30 controls delivery of stimulation at one amplitude during sleep, and controls delivery of stimulation at an increased amplitude upon detection of apnea or arousal to counter the increased intrinsic sympathetic activity associated with the apnea-arousal cycle. In some such embodiments, processor 30 controls delivery of stimulation at a first location during sleep, such as delivery via an electrode 18 located between the C1 and C2 vertebrae to increase parasympathetic activity and thus promote restful sleep and an open airway. In these embodiments, processor 30 controls delivery of stimulation at an additional or alternate location upon identification of an apnea or arousal, such as via an electrode 18 located between the T1 and T4 vertebrae in order to counter the increased intrinsic sympathetic activity associated with the apnea-arousal cycle.

Processor 30 continues to monitor physiological parameters to determine whether the state or arousal persists (110), and can modify the neurostimulation based on this determination (112). For example, processor 30 can increase the amplitude of neurostimulation to counteract a persistent arousal by further decreasing sympathetic outflow and/or increasing parasympathetic outflow to the heart of patient 12. Processor 30 can store information relating to identified apneas in memory 44 (114), and can use such information as feedback to improve the efficacy of IMD 14 (116), as described above.

Various embodiments of the invention have been described. For example, numerous techniques for treating effects of sleep apnea with neurostimulation have been described. Nevertheless various modifications can be made to the techniques described above. For example although IMD 14 is described herein as implanted within patient 12, IMD 14 may be external to patient 12 and coupled to electrodes 18 by a percutaneous lead.

Moreover, IMD 14 may comprise a radio-frequency (RF) neurostimulation system known in the art. Such systems include a processor and pulse generator located external to the patient that generates RF pulses under the control of the processor. In such systems, circuitry implanted with the patient and coupled to electrodes by a lead converts the RF pulses to electrical pulses that are delivered via the electrodes.

In some embodiments, a system for treating effects of sleep apnea with neurostimulation includes a plurality of devices. For example, a system according to the invention can include a first device for detecting sleep apnea, and a second device for delivering neurostimulation in response to a signal received from the first device indicating detection of apnea or arousal. In an exemplary embodiment, the first device is an implanted pacemaker that detects apnea and/or arousal based on electrical activity within the heart of a patient as described above. The pacemaker can indicate the detection to a second device, which takes the form of an implanted or external neurostimulator as described above, via radio frequency communication with the neurostimulator. The neurostimulator stimulates the spinal cord or other neural tissue, according to the techniques described above, in response to the indication. These and other embodiments are within the scope of the following claims.

The invention claimed is:

1. A method for treating effects of sleep apnea comprising stimulating a spinal cord of a patient at a predetermined location to modulate activity of an autonomic nervous system of the patient.

2. The method of claim 1, wherein stimulating the spinal cord of the patient comprises stimulating the spinal cord at a location between a first thoracic vertebrae and fourth thoracic vertebrae of the patient.

3. The method of claim 1, wherein stimulating the spinal cord of the patient comprises stimulating the spinal cord at a location between a first cervical vertebrae and a second cervical vertebrae of the patient.

4. The method of claim 1, wherein stimulating the spinal cord comprises stimulating the spinal cord via an electrode implanted within the patient proximate to the spinal cord.

5. The method of claim 1, wherein stimulating the spinal cord comprises delivering at least one of direct current and a pulse train via an electrode located proximate to the neural tissue.

6. The method of claim 1, wherein stimulating the spinal cord comprises at least one of stimulating the spinal cord at a location that reduces sympathetic nervous activity and stimulating the spinal cord at a location that increases parasympathetic nervous activity.

7. The method of claim 1, further comprising determining that the patient is asleep, and wherein stimulating the spinal cord comprises stimulating the spinal cord in response to the determination.

8. The method of claim 1, further comprising:
receiving a signal from a sensor that indicates a physiological parameter of the patient associated with an apnea condition; and
identifying the apnea condition based on the signal, and wherein stimulating the spinal cord comprises stimulating the spinal cord in response to the identification of the apnea condition.

9. The method of claim 8, wherein identifying the apnea condition comprises identifying an arousal state associated with the apnea condition.

10. The method of claim 8, wherein identifying the apnea condition comprises identifying the apnea condition based on at least one of:
a respiration rate, a respiration depth, a respiration pattern, a respiration rate variability metric, an identification of a Cheyne-Stokes respiration sequence, an oxygen level within blood, a carbon dioxide level within blood, a heart rate, a heart rate variability metric, a heart rate turbulence condition, a Q-T interval length, an S-T interval length, a blood pressure, an intracardiac pressure, an intrathoracic pressure, an activity level of a nerve associated with respiration.

11. The method of claim 8, wherein stimulating the spinal cord comprises modifying stimulation of the spinal cord in response to identifying the apnea condition.

12. The method of claim 11, wherein modifying stimulation comprises at least one of modifying a stimulation amplitude and stimulating the patient at another predetermined location.

13. The method of claim 8, further comprising modifying a stimulation signal to the spinal cord during a period of arousal associated with the identified apnea condition based on the physiological parameter.

14. The method of claim 8, further comprising:
storing at least one piece of information relating to at least one previously identified apnea condition;
modifying a neurostimulation parameter based on the at least one piece of information; and
delivering a neurostimulation signal according to the modified parameter in response to identification of a subsequent apnea condition.

15. A system for treating effects of sleep apnea comprising:
an electrode located at a predetermined site proximate a spinal cord of a patient; and
a processor coupled to the electrode to control delivery of an electrical stimulation therapy to the spinal cord via the electrode to modulate activity of an autonomic nervous system to treat effects of sleep apnea of the patient.

16. The system of claim 15, wherein the electrode is located between a first thoracic vertebrae and a fourth thoracic vertebrae of the patient.

17. The system of claim 15, wherein the electrode is located between a first cervical vertebrae and a second cervical vertebrae of the patient.

18. The system of claim 15, wherein the processor is coupled to an output circuit that is coupled to the electrode, and said processor controls the output circuit to deliver at least one of a direct current and a pulse train via the electrode.

19. The system of claim 15, wherein the processor determines that the patient is asleep, and said processor controls delivery of the electrical stimulation therapy to the spinal cord in response to the determination.

20. The system of claim 19, further comprising a sensor to generate a signal based on at least a one of: a posture of the patient, an activity level of the patient, a snoring sound of the patient, and wherein the processor determines that the patient is asleep based at least in part on the signal.

21. The system of claim 19, further comprising a patient programmer and wherein the processor determines that the patient is asleep by receiving from the patient programmer an indication that the patient intends to sleep, and further comprising:
means for initiating a decremental time or an incremental timer in response to receiving the indication; and
wherein the processor causes delivery of the electrical stimulation therapy in response to expiration of the decremental timer or the incremental timer.

22. The system of claim 15, further comprising a sensor to generate a signal that indicates a physiological parameter of the patient, and wherein the processor identifies an apnea condition based on the signal and controls delivery of the electrical stimulation therapy to the spinal cord in response to the identification.

23. The system of claim 22, wherein the physiological parameter indicates arousal associated with apnea, and the processor identifies the apnea condition by identifying an arousal associated with apnea.

24. The system of claim 22, wherein processor identifies the apnea condition based at least in part on at least a one of:
a respiration rate, a respiration depth, a respiration pattern, a respiration rate variability, an identification of a Cheyne-Stokes respiration condition, an oxygen level within a body fluid, an oxygen level within a volume of blood, a carbon dioxide level within the volume of blood, a heart rate, a heart rate variability index, a heart rate turbulence condition, a Q-T interval length, an S-T interval length, a blood pressure, an intracardiac pressure, an intrathoracic pressure, a sound associated with a snoring condition, an activity level of a nerve associated with respiration.

25. The system of claim 22, wherein the processor is coupled to an output circuit that is coupled to the electrode, and wherein said processor controls the output circuit to modify the electrical stimulation therapy of the spinal cord in response to the identification.

26. The system of claim 25, wherein the processor controls the output circuit to modify an amplitude of the electrical stimulation therapy.

27. The system of claim 25, wherein the electrode comprises a first electrode located at a first predetermined site, the system further comprising a second electrode located at a second predetermined site, and
wherein the processor controls the output circuit to provide the electrical stimulation therapy to the spinal cord via the second electrode.

28. The system of claim 22, wherein the processor is coupled to an output circuit that is coupled to the electrode, and controls the output circuit to modify the electrical stimulation therapy of the spinal cord during an arousal event associated with the identified apnea condition based on the physiological parameter.

29. The system of claim 22, further comprising a memory coupled to the processor, wherein the processor is coupled to an output circuit that is coupled to the electrode, and
wherein the processor stores information relating to at least one previously identified apnea condition in the memory, and the processor modifies a neurostimulation parameter based on the information, and controls the output circuit to deliver neurostimulation according to the modified parameter in response to identification of a subsequent apnea condition.

30. The system of claim 15, wherein the electrode is a first electrode coupled and the processor is a first processor coupled to the first electrode via a first output circuit, the system further comprising a second processor and a second electrode located proximate to a heart of the patient coupled to the second processor via a second output circuit, and
wherein the first processor controls the first output circuit to deliver electrical stimulation therapy to the spinal cord and the second processor controls the second output to deliver pacing pulses to the heart.

31. The system of claim 15, wherein at least one of the electrode and the processor are implanted within the patient.

32. A method for treating effects of sleep apnea comprising:
stimulating a portion of neural tissue of a patient transcutaneously via an electrode in contact with the patient's skin at a predetermined location to modulate activity of an autonomic nervous system of the patient.

33. The method of claim 32, wherein stimulating the portion of neural tissue comprises transcutaneously stimulating the portion of neural tissue via an electrode located within a dermatome associated with an area of a spinal cord of the patient between a first thoracic vertebrae and fourth thoracic vertebrae of the patient.

34. The method of claim 32, wherein transcutaneously stimulating neural tissue comprises transcutaneously stimulating the portion of neural tissue via an electrode located within a dermatome associated with an area of a spinal cord of the patient between a first cervical vertebrae and a second cervical vertebrae of the patient.

35. The method of claim 32, wherein transcutaneously stimulating the portion of neural tissue comprises transcutaneously stimulating the portion of neural tissue via an electrode proximate to an ear of the patient.

36. The method of claim 32, further comprising determining whether the patient is asleep, and wherein transcutaneously stimulating the portion of neural tissue comprises transcutaneously stimulating neural tissue in response to a positive determination that the patient is asleep.

37. The method of claim 32, further comprising:
receiving a signal from a sensor that indicates a physiological parameter of the patient associated with an apnea condition; and
identifying the apnea condition based on the signal, and wherein transcutaneously stimulating the portion of neural tissue comprises transcutaneously stimulating the portion of neural tissue in response to the identification of the apnea condition.

38. The method of claim 37, wherein identifying the apnea condition comprises identifying an arousal associated with the apnea condition.

39. The method of claim 37, wherein identifying the apnea condition comprises identifying the apnea condition based on at least one of:
a respiration rate, a respiration depth, a respiration pattern, a respiration rate variability, an identification of Cheyne-Stokes respiration, an oxygen level within blood, a carbon dioxide level within blood, a heart rate, a heart rate variability, a heart rate turbulence, a Q-T interval length, an S-T interval length, a sound associated with a snoring condition, a blood pressure.

40. The method of claim 37, wherein transcutaneously stimulating the portion of neural tissue comprises modifying stimulation in response to the identification.

41. The method of claim 37, further comprising modifying the electrical stimulation therapy during a period of arousal associated with the identified apnea condition based on the parameter.

42. The method of claim 37, further comprising:
storing information relating to at least one previously identified apnea condition;
modifying a parameter of neurostimulation based on the information; and
delivering neurostimulation according to the modified parameter in response to identification of a subsequent apnea condition.

43. A system for treating effects of sleep apnea comprising:
an electrode located at a predetermined site on and in contact with a surface of the skin of a patient; and
a processor coupled to the electrode to control transcutaneous delivery of electrical stimulation therapy from the electrode to a portion of neural tissue of the patient to modulate activity of an autonomic nervous system of the patient.

44. The system of claim 43, wherein the electrode is located within a dermatome associated with an area of a spinal cord of the patient between a first thoracic vertebrae and a fourth thoracic vertebrae of the patient.

45. The system of claim 43, wherein the electrode is located between a first cervical vertebrae and a second cervical vertebrae of the patient.

46. The system of claim 43, wherein the electrode is located proximate a portion of an ear of the patient.

47. The system of claim 43, wherein the processor determines whether the patient is asleep, and controls transcutaneous delivery of stimulation in response to a determination that the patient is asleep.

48. The system of claim 43, further comprising a sensor to generate a signal that indicates a physiological parameter of the patient, wherein the processor identifies an apnea condition based on the signal and controls a transcutaneous delivery of electrical stimulation therapy in response to the identification.

49. The system of claim 48, wherein the physiological parameter indicates an arousal associated with the apnea condition, and the processor identified the apnea condition by identifying the arousal associated with apnea condition.

50. The system of claim 48, wherein the processor processes the signal to identify the apnea based on at least a one of:
a respiration rate, a respiration depth, a respiration pattern, a respiration rate variability, an identification of Cheyne-Stokes respiration, an oxygen level within a volume of blood, a carbon dioxide level within a volume of blood, a heart rate, a heart rate variability, a heart rate turbulence, a Q-T interval length, an S-T interval length, a sound associated with a snoring condition, a blood pressure.

51. The system of claim 48, wherein the processor is coupled to an output circuit that is coupled to the electrode, and the processor controls the output circuit to modify the electrical stimulation therapy in response to the identification.

52. The system of claim 48, wherein the processor is coupled to an output circuit that is coupled to the electrode, and the processor controls the output circuit to modify the electrical stimulation therapy during a period of arousal based on the parameter.

53. The system of claim 48, further comprising a memory coupled to the processor, wherein the processor is coupled to an output circuit that is coupled to the electrode, and
wherein the processor stores information relating to an identified apnea condition in the memory, modifies a neurostimulation parameter based on the information, and controls the output circuit to deliver neurostimulation therapy according to the modified parameter in response to detection of a subsequent apnea condition.

54. A system comprising:
means for producing stimulation,
means for delivering the stimulation to a spinal cord of a patient at a predetermined location to modulate activity of an autonomic nervous system of the patient, and
means for identifying an apnea condition, wherein the means for producing stimulation produces the stimulation in response to identification of an apnea condition.

55. The system of claim 54, wherein the means for delivering the stimutation to the spinal cord comprises means for transcutaneously stimulating at least one nerve that couples to the spinal cord.

56. The system of claim 54, further comprising means for determining whether the patient is asleep, wherein the means for producing the stimulation produces the stimulation based on the determination.

57. The system of claim 54, wherein the means for delivering the stimulation comprises means for stimulating at least one of peripheral nerves and muscle tissue that couple to the spinal cord.

* * * * *